United States Patent [19]

Sueptitz

[11] Patent Number: Plant 6,591

[45] Date of Patent: Feb. 7, 1989

[54] CHRYSANTHEMUM PLANT NAMED GOLDEN ANTONIO

[75] Inventor: Dieter Sueptitz, Hamburg, Fed. Rep. of Germany

[73] Assignee: Ball Pan Am Plant Co., Parrish, Fla.

[21] Appl. No.: 74,482

[22] Filed: Jul. 16, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Golden Antonio, characterized by its yellow-gold flower color, daisy form, nine week response, free breaking habit, good performance in year round pot mum programs.

1 Drawing Sheet

The present invention comprises a new and distinct cultivar of *Chrysanthemum morifolium,* Ramat., hereinafter referred to by the cultivar name Golden Antonio.

Golden Antonio is a natural mutation of Antonio and was discovered by Dieter Sueptitz in 1985 in Hamburg, Federal Republic of Germany. The new cultivar was discovered while growing among flowering plants of the parent cultivar in greenhouses in Hamburg, Federal Republic of Germany. The new cultivar was immediately recognized by its clear bright yellow-gold daisy flowers, as opposed to the white flower color of Antonio.

The first act of asexual reproduction of Golden Antonio was accomplished when vegetative cuttings were taken from the initial selection in 1985 in a controlled environment in Hamburg, Federal Republic of Germany by a technician working under formulations established and supervised by Dieter Sueptitz. Horticultural examination of selected units initiated in 1985 has demonstrated that the combination of characteristics as herein disclosed for Golden Antonio are firmly fixed and are retained through successive generations of asexual reproduction.

The following traits have been repeatedly observed and are determined to be basic characteristics of Golden Antonio, which in combination distinguish this Chrysanthemum as a new and distinct cultivar:

1. Daisy pot mum, flat capitulum form, single capitulum type.
2. Clear yellow ray florets.
3. Mature disc florets yellow, immature disc florets lime green.
4. Nine week flowering response.
5. Capitulum 55–65 mm across, ray florets up to 28 mm long and 12 mm wide.
6. Approximately 26 ray florets per capitulum.
7. Performs well in year round pot mum programs.
8. Free breaking habit.

Golden Antonio has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Golden Antonio is Brightlight, disclosed in U.S. Plant Pat. No.

5,778. In comparison to Brightlight, Golden Antonio has a more compact habit, one week slower flower response, slightly smaller flower diameter, a much deeper yellow-gold flower color, and it performs better in northern winter flowerings. Golden Antonio is similar to its parent Antonio except for the bright yellow-gold flower color of the new cultivar.

The accompanying photographic drawing shows typical inflorescence and foliage characteristics of Golden Antonio. The photograph is in black and white, with a few flowers being colored to accurately depict true flower color.

In the following description, color references are made to the Royal Horticultural Society Colour Chart. The color values were determined between noon and 1:00 p.m. on Sept. 24, 1986 under fluorescent light at Parrish, Fla.

Classification:

*Botanical.*—*Chrysanthemum morifolium,* Ramat., cv. Golden Antonio.

*Commercial.*—Daisy pot.

INFLORESCENCE

A. Capitulum:

*Form.*—Flat.

*Type.*—Single.

*Diameter across face.*—55–65 mm.

B. Corolla of ray florets:

*Color (general tonality from a distance of three meters).*—Yellow.

*Color (upper surface).*—5A.

*Color (under surface).*—5C.

C. Corolla of disc florets:

*Color (mature).*—Yellow.

*Color (immature).*—Light lime green.

D. Reproductive organs:

*Androecium.*—Present in disc florets only.

*Gynoecium.*—Present in both disc and ray florets.

PLANT

A. General appearance:

*Height.*—22–25 cm from the edge of the pot, the height varies depending upon growing conditions.

B. Foliage:

*Color (upper surface).*—147A.

*Color (under surface).*—147B.

*Shape.*—Ovate, with cleft leaf margins.

I claim:

1. A new and distinct cultivar of Chrysanthemum plant named Golden Antonio, as illustrated and described, and particularly characterized by its yellow-gold flower color, daisy form, nine week response, free breaking habit, and its good performance in year round pot mum programs.

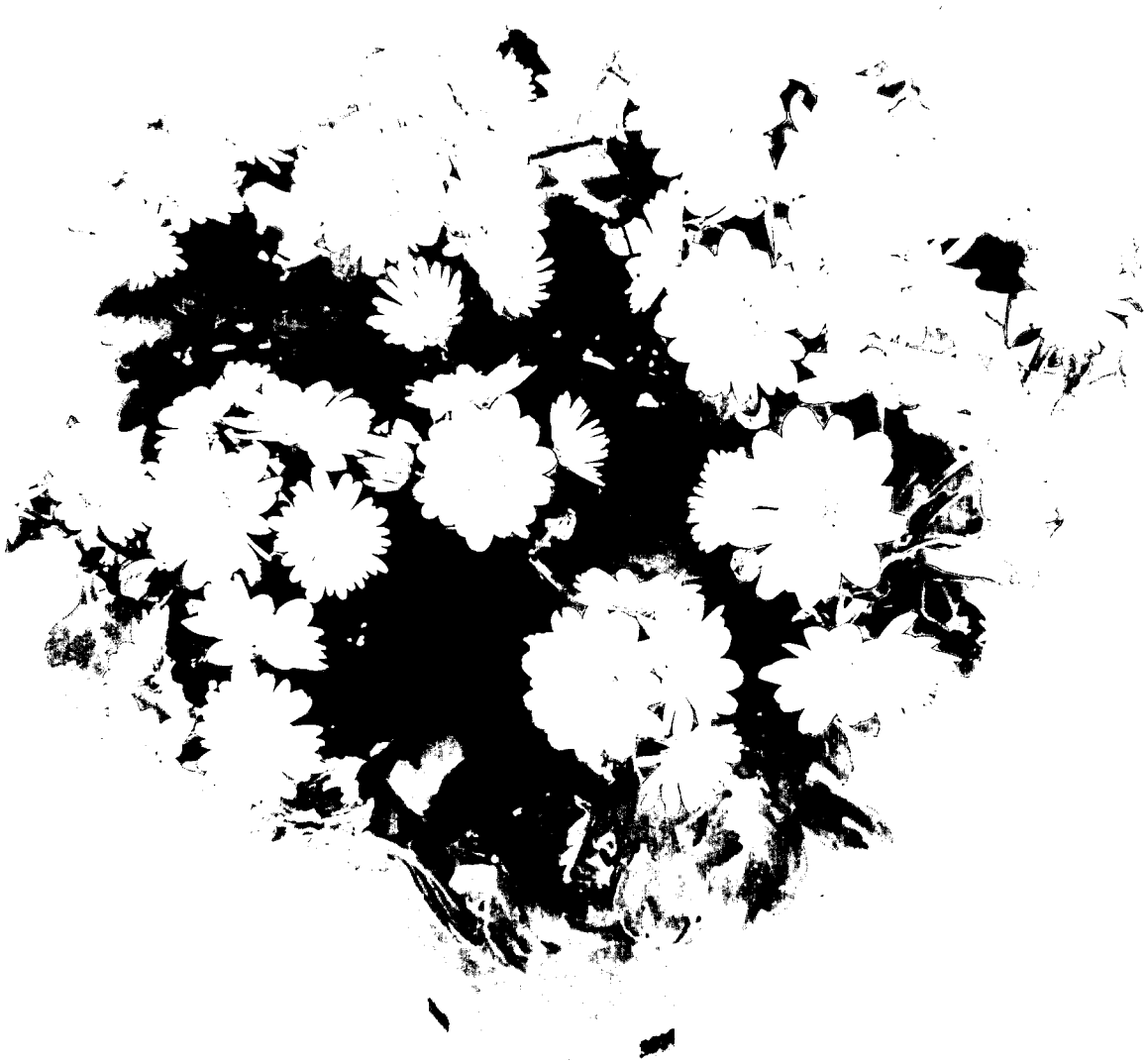

* * * * *